United States Patent [19]

Eschmann

[11] 4,019,506
[45] Apr. 26, 1977

[54] RIGID SUPPORTING BANDAGE AND METHOD FOR APPLYING SAME

[76] Inventor: Peter Eschmann, 82 Weinbergstrasse, 8006 Zurich, Switzerland

[22] Filed: Mar. 8, 1976

[21] Appl. No.: 665,052

[30] Foreign Application Priority Data

Mar. 14, 1975 Switzerland ............ 3168/75

[52] U.S. Cl. ................ 128/90; 128/91 A; 128/156
[51] Int. Cl.² .............................. A61F 5/04
[58] Field of Search ............ 128/90, 89, 155, 156, 128/91 A, 87 R; 428/221, 236, 245, 246, 289, 290

[56] References Cited

UNITED STATES PATENTS

| 2,969,791 | 1/1961 | Ekenstam et al. ............ 128/90 |
| 3,373,741 | 3/1968 | Hill et al. ............ 128/90 |
| 3,656,475 | 4/1972 | Hanrahan, Jr. ............ 128/90 |
| 3,692,023 | 9/1972 | Phillips et al. ............ 128/90 |
| 3,935,355 | 1/1976 | Kuhn ............ 128/156 X |

Primary Examiner—John D. Yasko

Attorney, Agent, or Firm—Gilbert L. Wells; Heinrich W. Herzfeld

[57] ABSTRACT

A rigid supporting bandage is described which is applied in situ for fixing and repositioning a part of the live body which is at least partly covered with skin, and which bandage comprises
 a. a flexible layer of textile material,
 b. an outer layer of hard self-cured synthetic polymer resin on the outside of the bandage, and
 c. an intermediate layer of meshes of textiles filled with the same hard polymer resin as constitues the outer layer. At least the innermost ply of meshes of the base layer must be free from the resin. The base layer has at least one front end uncovered by the intermediate and outer layers, and contains channels which open at the one front end to the outside of the bandage. These channels are covered, on the side of the body part, by the innermost polymer resin-free ply of meshes of the base layer.

A method for applying this bandage is also described.

21 Claims, 11 Drawing Figures

RIGID SUPPORTING BANDAGE AND METHOD FOR APPLYING SAME

The invention relates to a rigid supporting bandage or a rigid part of a bandage which is suitable, by application in situ, for fixing and repositioning a part of the body, which is at least partially covered with skin, and comprises a base layer of textile material which adapts itself to the shape of the underlying part of the body, an intermediate layer on top of the base cover and optionally joined to the latter and a polymer layer which surrounds the intermediate layer, has a substantially uniform rigidity and consists of a chemically hardened, rigid plastic composition.

A bandage of this type is known from German Offenlegungsschrift 2,015,534 published in print on Mar. 11, 1971 and from GDR Patent Specification 86,674.

In these known bandages, however, the intermediate layer consists of a barrier layer, which is intended to cover the base layer and should normally be flexible, and of a preformed film of plastic or sheet of synthetic material, which is intended to be located between the base layer and the polymer (synthetic resin) layer, the latter forming an outer cover of the bandage, and should be neutral or inert towards these layers and impermeable to liquid. Suitable barrier layers which are inert towards most synthetic resin compositions, and the solvents contained therein, are rubber-like films or sheets of synthetic rubber balloon compositions, owing to their unreactive nature and their elasticity, and also loose polyethylene films, polypropylene films and other films.

In practice, the following points have proved decisive for the usefulness and applicability of a supporting bandage:

1. Respiration of the skin (problems of perspiration and transpiration of the skin).
2. The problem of opening the bandage.
3. Protection of the skin and protection of the entire body against the resorption of harmful substances into the metabolism.
4. Handiness for personnel working with the bandage (time required, simplicity, little diversification of material, degree of soiling and the like).
5. The scope which remains, in spite of the supporting bandage, for therapy (drainage, irrigation, radiotherapy, nuclear therapy and the like) and diagnosis (transmission of x-rays, xerography and ultrasonic diagnostics).
6. Factors which are relatively difficult to estimate but are all the more important, such as psycho-social effects, purely psychological effects and effects on the physiology of healing: this means all those factors which modify any healing process or protective process which occurs, that is to say accelerate or retard it.

Practical experience has shown that, for example, excessively thin and light supporting bandages, which hardly handicap the bearer in any way, produced the effect that the increased mobility, restlessness and non-physiologically activated metabolism, which such bandages produce, adversely affect the desired healing process or protective process.

Amongst these requirements, the known bandage does not satisfactorily fulfil those for practically unhindered respiration of the skin and hence adequate ventilation and for the drawing away of water vapour and transpiration products. For, either the meshes of the textile material of the base layer are chosen so that they are wide enough to ensure satisfactory respiration of the skin and then the base layer lacks the necessary density in order to achieve a satisfactory fixation, for example of a broken limb, when the plastic cures, or, if the mesh width and the density of the textile material suffice for a satisfactory fixation, satisfactory respiration of the skin is not ensured, but at most some microcirculation of air, for example through small air spaces between uncut loops of the pile of a terry cloth (rough towel).

It is therefore the object of the invention to provide a rigid supporting bandage or part of a bandage, which, coupled with a simpler construction, achieves good fixation and repositioning and, at the same time, completely satisfactory ventilation of the skin of the part of the body.

This is achieved by means of a rigid bandage or part of a bandage of the type initially described, which is characterised in that a. the polymer layer has been produced by applying a layer of not yet cured, self-curing prepolymer material to the base layer of textile material, which has already been applied to the part of the body and is still free from plastic or plastic-forming catalysts, and by subsequent curing, whereby the polymer layer has penetrated at least partially into meshes of the outer plies of the textile material, forming the intermediate layer, b. the base layer of textile fabric consists of an inner ply, facing the part of the body, and at least one outer ply of textile fabric, the mesh width of the textile material being so small and the base layer being so thick that, when the prepolymer material partially penetrates into the base layer, at least one ply of the base layer, which is in direct, continuous contact with the skin of the part of the body, remains free from propolymer material or cured plastic and hence remains non-rigid, and c. within the ply of the base layer, which is free from prepolymer or cured plastic, channels are provided which open at least at one front end of the base layer, preferably run substantially parallel to the part of the body and are everywhere separated from the surface of the part of the body by an innermost ply of textile material, free from plastic.

Preferably the cured polymer layer is formed from the prepolymer material within less than 30 minutes.

The preferred prepolymer materials are: cold-catalysed pre-polymerised polyacrylate casting resin, flexible polyester mixture with a fast "cold" catalyst system, dihydroxy- or polyhydroxy-diisocyanate or -polyisocyanate compounds (PU) built up in most cases from cross-linked polyesters or polyethers or from polyacetals and in the form of a reactive casting resin or a foam, plasticised epoxide foam materials, epichlorohydrin/bisphenol A copolymers, copolymers based on styrene, copolymers based on methacrylic acid or its methyl ester, maleic acid glyptalkyds, styrene/ethylene glycoloids, butyl acrylate/butylacrylamides, vinyl acetate/stearate derivatives and a crosslinkable hydrocarbon casting resin with a redox system.

The textile material can consist of a woven fabric, a knitted fabric or a non-woven material (fleece).

Preferably the outward-facing textile layer here has so large a mesh width that the prepolymer material can readily penetrate into the layer and the latter is intimately joined to the plastic composition after the prepolymer has cured.

The textile layer can consist of a close-meshed textile carrier of natural fibre materials or suitable synthetic fibres, preferably of knitted cotton stretch-fabric of sufficient denseness. A textile material is "close-meshed" in the sense of the invention of it represents a barrier to the prepolymer material, which prevents penetration of the latter right through to the skin. The critical mesh width must be determined experimentally for each layer of textile material and depends on the prepolymer used and on the layer thickness.

The ply of the textile layers, which is closest to the skin and which can consist of, for example, knitted cotton stretch-fabric or interlock weighing 170 g/m$^2$, can be converted, by means of a flat special seam, to a tubular bandaging material or can also be left in a sheet-like state.

In the case of multi-ply textile base layers the outermost layer of the textile carrier can be loose and the material can preferably be net-like and elastic. "Loose" here means that this textile ply does not represent a barrier to the prepolymer material.

The outermost loose textile layer can also be chemically pre-finished in a non-curing manner so that the eventual chemical curing reaction with the still reactive plastic curing mixture (prepolymer material) applied can take place more rapidly and give a stronger chemical bond.

The channels for the respiration of the skin or for treating the bandaged part of the body through the finished bandage are preferably located between an inner ply free from plastic and an outer, adjacent ply of the textile layer. In specially indicated cases the channels can also be accommodated, in a manner which is in itself known, directly on the skin and underneath the innermost textile layer.

The channels can also have the form of passages comprising small tubes of an elastic plastic material, which preferably extend in the longitudinal direction of the part of the body; suitable plastic materials for the small tubes are, in particular, polyvinyl chloride, polyethylene or polypropylene.

The channels in the textile layer free from plastic can be produced by inserting removable small plastic tubes or plastic rods which are pulled out of the finished rigid bandage, or part of the bandage, after its application.

Preferably the outermost ply, impregnated with cured plastic, of the textile layer, contains at least one wire which preferably extends in the longitudinal direction of the part of the body and which consists of metal, plastic or a textile material of sufficient tensile strength so that, using this wire as a means of opening, the cured plastic layer of the rigid supporting bandage can be severed.

The insertable opening wire preferably consists of plastic, thread, twist or plastic string, preferably nylon string; the plastic string is preferably finished with a self-adhesive substance. For example, it can consist of a X-ray-positive plastic.

Such a metal wire or conductive plastic wire for opening the cured plastic shell can also be connected to a source of electric current, preferably direct current of a certain amperage, so that in this way the hard supporting plastic shell can be cut open by means of a current in the manner of a "thermal saw".

The cured plastic layer can, however, also be of a type which can be severed by a normal knife, a metal spatula or by ordinary scissors.

Preferably the thickness of the plastic layer should be at least 1 mm in the cured state.

The textile layer and the cured plastic layer can be translucent to X-rays, and other rays necessary for diagnostic or therapeutic purposes, to the extent of at least 50–80% or even greater.

It is possible to insert a padding material between the surface of the skin and the first ply of the textile layer or between two plies of the textile layer, either by loosely squeezing this padding material between the textile plies or by applying the padding material to one of the textile plies, so that the formation of pressure sores on the part of the body, or on the skin thereof, by the supporting bandage can be avoided.

The various indicated plies of the textile layer, the means of providing a passage, the means of opening and, if appropriate, protective means, that is to say all the elements of the bandage with the exception of the outermost plastic layer to be cured, can be combined in one single article consisting of a multi-layer composite textile carrier tubing or of multi-layer composite bandage (in the case of flat supporting bandages).

During the initial stage of hardening it is possible to place upon the plastic mixture which is still in a semi-liquid or almost rigid state, a hardening foil, glass fibre fabric or similar reinforcing agent, which soon combines with the curing mixture or is intimately jointed to the latter and which can optionally be coated with a further plastic layer which can then be cured; thus, substantial reinforcement is possible at points of the supporting bandage which are particularly subject to physical stresses and loads, for example in the load lines in the case of a supporting cast which enables the patient to walk, or of a pelvic supporting cast.

In order to achieve improved external shaping it is possible to use synthetic plastics sheets which have a certain separating action relative to the hardenable synthetic resin mixture, are relatively flexible and elastic and, during the curing period, and preferably during the semi-rigid reaction phase of the plastic mixture, can be spread and wrapped from the outside like a foil over and around the plastic mixture; as a result, a proper casting mould or a tubular film is not required in order to obtain a pleasing external shape; the process can be used with cylindrical and tubular as well as sheet-like supporting casts (bandages), is simple and can be used even in extreme situations.

For the purpose of protection against external electromagnetic rays, corpuscular rays or other types of rays, one or more additives can be admixed to the plastics layer of the bandage, or an intermediate layer can be inserted into the cast or bandage so that the supported part of the body is protected as far as possible from these external rays, either by absorption of the greatest possible percentage of these external rays or by reflection.

A small pocket or a small compartment can be fitted on the surface of the hardening, or already cured, synthetic plastics layer; this pocket or compartment preferably consists of a transparent plastic material and a card or other information about the bearer of the supporting cast or bandage can be inserted therein so that useful information can rapidly be seen.

The fact that the supporting cast or bandage, or part of a supporting bandage, according to the invention, is "rigid" and "hard" in the finished, fully reacted state means that the bandaged part of the body can no longer be moved at the joints to be immobilised after the supporting bandage has been applied, and it means further that a certain retaining function is fulfilled and that this supporting bandage offers a certain protection against external physical or chemical influences.

Thus, the complex of the textile layer combined with the plastic layer provides the immobilised part of the body with an ideal heat insulation from the surrounding environment since, on the one hand, the plastic layer regulates the outward radiation of heat and, on the other hand, an excessive build-up of heat underneath the supporting bandage is avoided by the physiological circulation of the air within.

The innermost textile layer can be pre-finished with special substances and materials for the purpose of a possible therapy or of providing means of diagnosis.

The supporting bandage, or part of a supporting bandage, according to the invention allows drainage hoses for drawing-off, tubes for irrigation, for nourishing or for other therapeutic or diagnostic interventions, for feeding-in and drawing-off, or cooling tubes, for example for the local treatment of highly septic inflammatory local conditions, to be inserted in a very simple manner underneath the hardening, or cured, plastic shell.

Corrections or other alterations of the finished hard supporting bandage can also be carried out in situ and preferably in such a way that it is not necessary to destroy, or take off, the entire finished supporting bandage or the entire outer hard plastic layer.

In the case that corrections or other alterations of the finished hard supporting bandage, or part of a supporting bandage, are carried out a plastic layer which is applied subsequently is then able to combine as intimately as possible with the outermost textile layer and with the already fully cured plastic layer.

A further advantage of the supporting bandage, or part of a supporting bandage, according to the invention is that the tubular bandage principle (as is preferably used for the limbs) does not have to be used as an indispensible carrier material; when correspondingly suitable sheet-like carrier materials are used, it is likewise possible readily to apply sheet-like structures of supporting bandage, and highly complicated shaped stiffeners can also be produced.

Of course, such a bandage can also be applied when there is no real intention of fixing or repositioning the part of the body but protection of the part of the body against external physical or chemical influences from the surrounding environment is the prime object.

The rigid supporting bandage, or rigid part of a bandage, according to the invention can also be formed, in emergency situations (war events, disasters or necessary immediate measures), by applying the plastic mixture, which is to be cured on, directly to the layers of clothing on the part of the body to be immobilised, the clothes usually being discarded later on; thus, immobilisation, and partial pain-relief resulting therefrom, and under certain circumstances also a considerable stemming of blood, become possible.

All the components necessary for making a standard finished (emergency) supporting bandage according to the invention can be contained in a small handy pack, that is to say the plastic carrier complex with means of passage and means of opening, the necessary quantity of prepolymer components, activator systems which may be required, the implements for mixing and application and an optional extra outer protective film which is not an essential part of the bandage, optional protective layers for the inner layer of the bandage and optional agents for inhibiting the polymerisation, so that the whole represents a so-called "emergency pack" and so that even a layman can apply an immobilising, temporary supporting bandage in emergency situations (theatres of war or accidents) and considerable pain-relief and transportability is thus achieved.

Similar standard packs, either for once-only use or for repeated use, can also be made up for medical personnel (chiefly for such persons who are not very often required to make supporting bandages, for example general practitioners, personnel in small outpatient departments, casualty doctors and nurses).

Further details of the invention emerge from the description, which follows, of preferred embodiments of the invention, in conjunction with the attached drawing in which FIG. 1 shows a diagrammatic perspective representation of a first embodiment of the rigid supporting bandage according to the invention, applied to an arm, having ventilation channels and provided with a "thermal saw";

Figure 1:
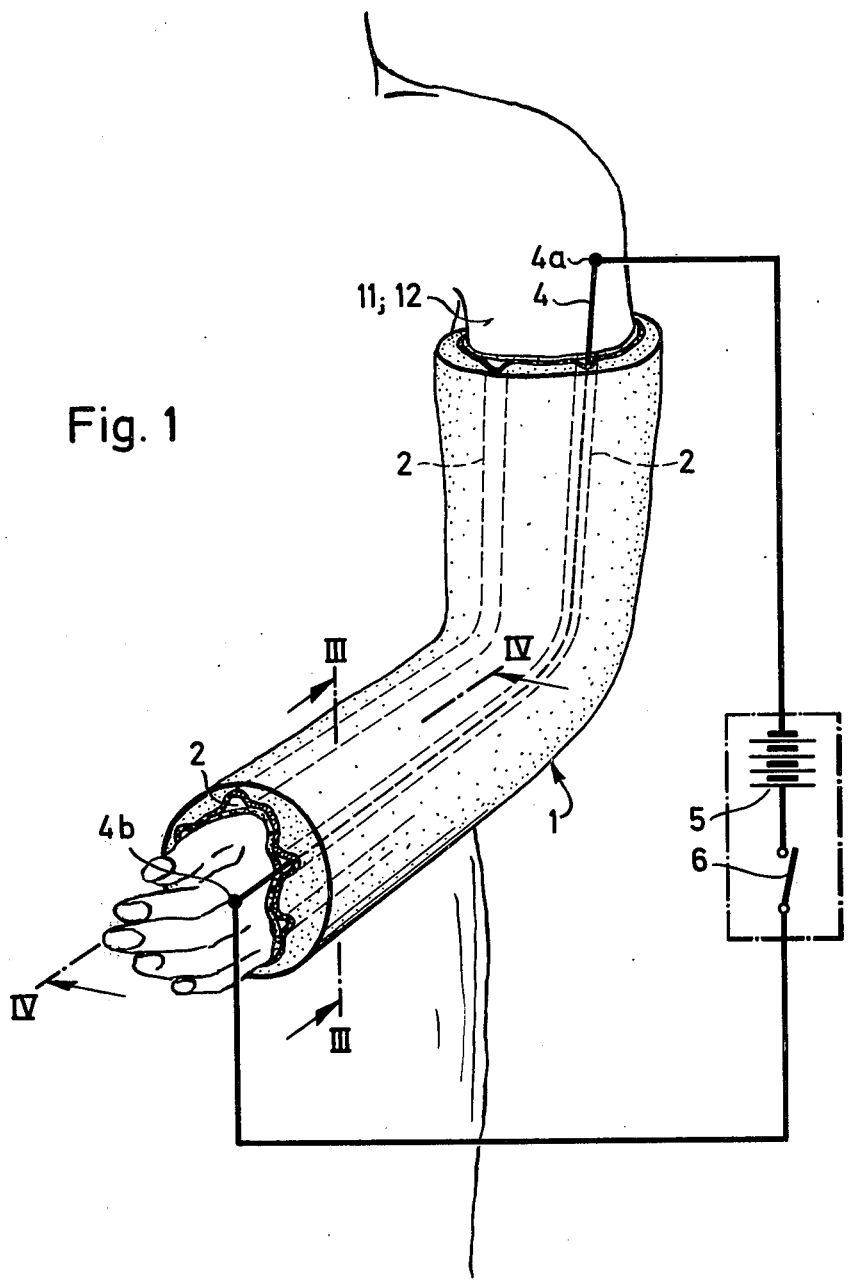
Figure 2:
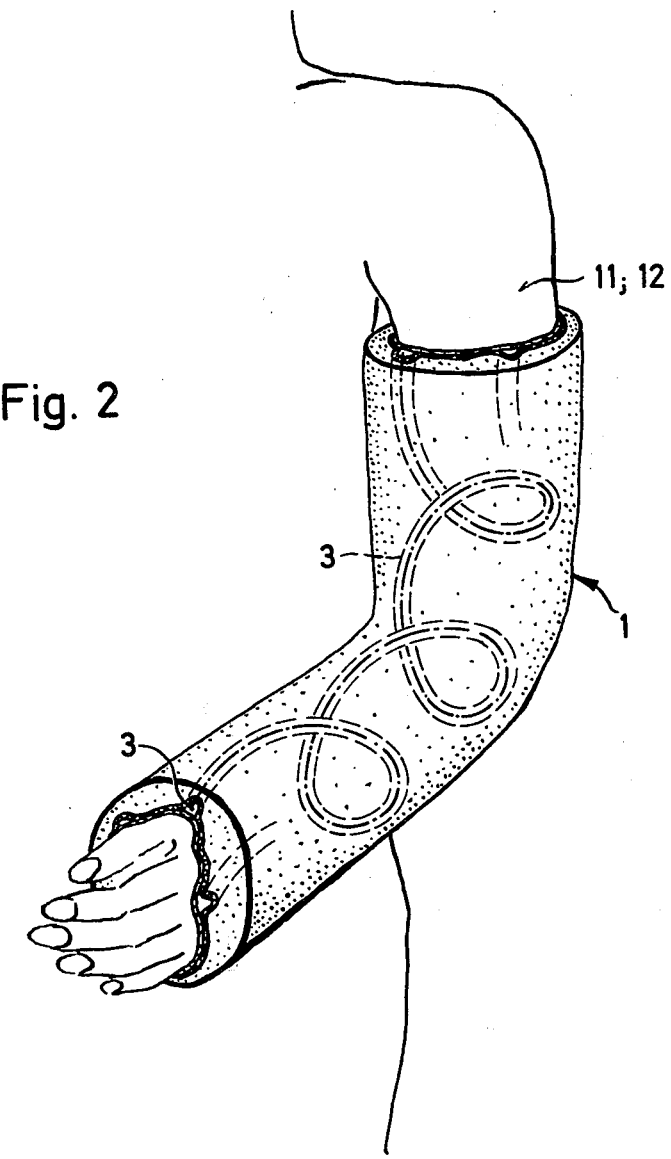
FIG. 2 shows an embodiment similar to that in FIG. 1, likewise in a perspective representation, but with a different arrangement of the ventilation channels.

In FIGS. 1 and 2 the rigid supporting bandage 1 is applied to the arm of the patient. In the embodiment according to FIG. 1 the ventilation channels 2 run parallel to the longitudinal direction of the arm, whilst the ventilation channels 3 in the embodiment according to FIG. 2 are wound around the arm.

In the supporting bandage according to FIG. 1 there is provided a severing wire 4, the ends 4a and 4b of which are connected to a current source 5 which heats the wire when the switch 6 is actuated, so that the outer layer of the bandage can be severed by means of the hot wire.

In the partial views, shown in FIGS. 3 to 8, of a similar embodiment a base layer 7 of textile material consists of the three plies 8, 9 and 10. This base layer 7 is drawn, for example in the form of a three-ply textile tubing, over the bare skin 11 of an arm 12. During the application a plastic cannula 13 is inserted between the inner-most ply 8 and the middle ply 9. The base layer 7 is here shown cut open in three steps. A prepolymer material 9 has penetrated into the outermost ply 10, which preferably consists of loose fabric which has wider meshes then the two other textile plies, up to its interface with the middle ply 9, whilst the middle ply 9 has not been penetrated. After hardening this prepolymer material forms a plastic layer 14, which, in addition to the outer hard pure plastic ply 15, also comprises the outermost textile ply 10 which has been penetrated by cured plastic.

On the outermost surface of the textile ply 10 there are threads or wires 16 and 17 embedded in the cured plastic. The textile-free plastic layer 15 can be torn open by means of these wires or threads. If the wires 16 and 17 are conductive, it is also possible to use them, after connecting the wires to a source of electric current as in FIG. 1 and after heating the wires, to cut the plastic layer 15 open by means of the "thermal saw" thus obtained. The three plies 8, 9 and 10 of the textile layer 7 can then easily be cut open with scissors.

Figure 4:
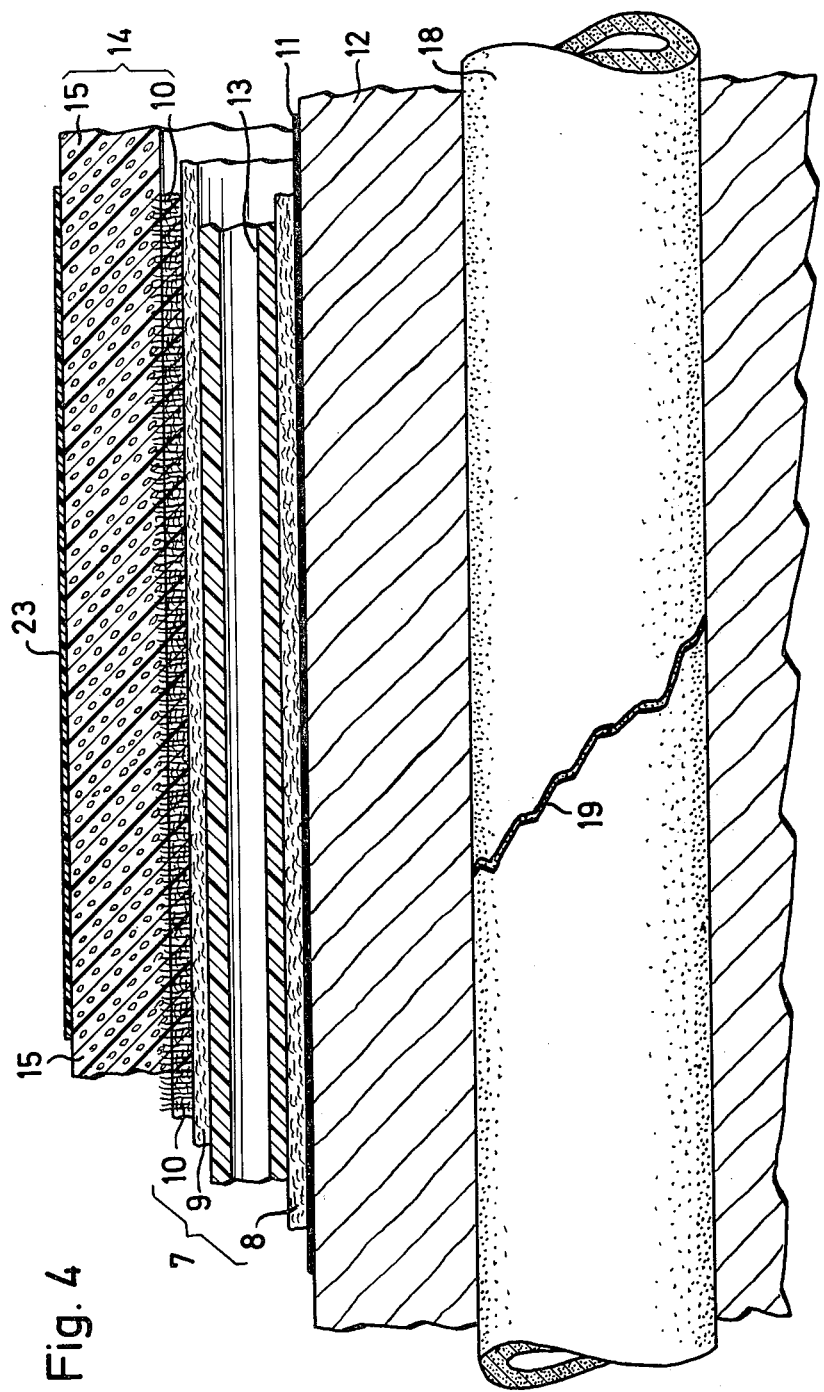
FIG. 4 shows a partial view of a longitudinal section of a plane indicated by IV—IV in FIG. 1.
Figure 5:
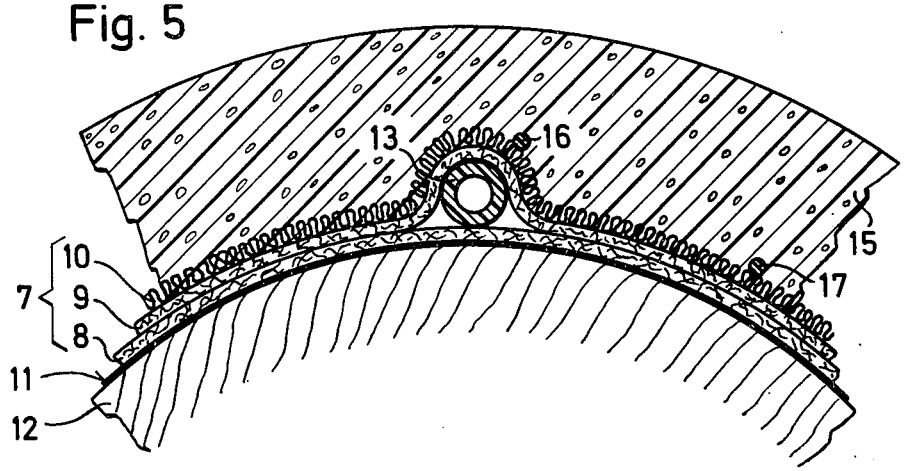
FIG. 5 shows a partial view in cross-section of the same embodiment as in FIG. 3.

FIG. 4 also shows a bone 18 of the arm 12 with the site of fracture 19.

Figure 6:
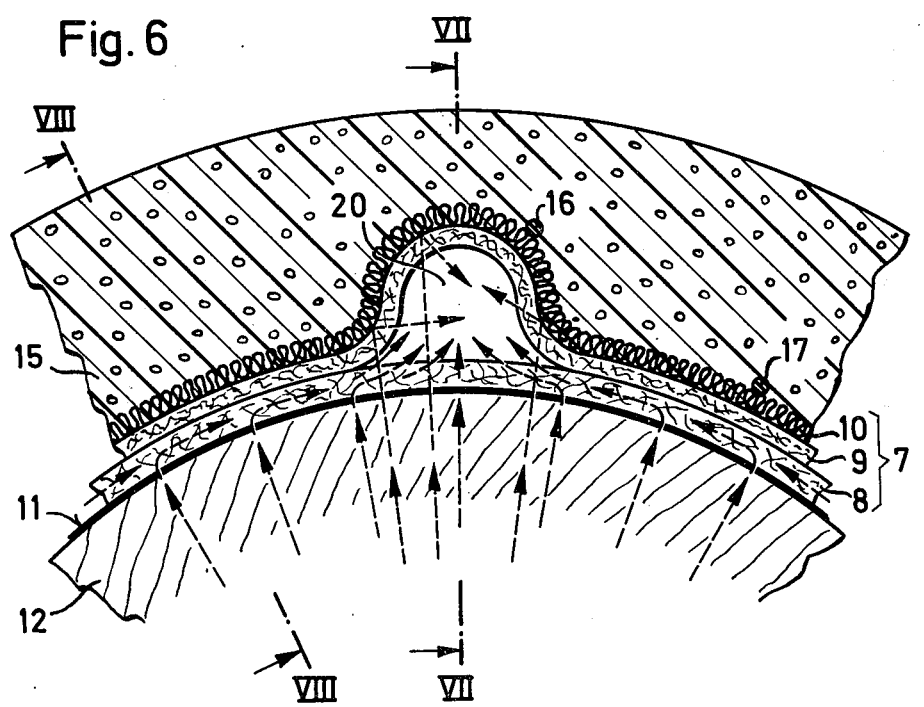
FIG. 6 shows the same view as in FIG. 5 in an enlarged form, after removing the cannula used to form the ventilation channel.
Figure 7:
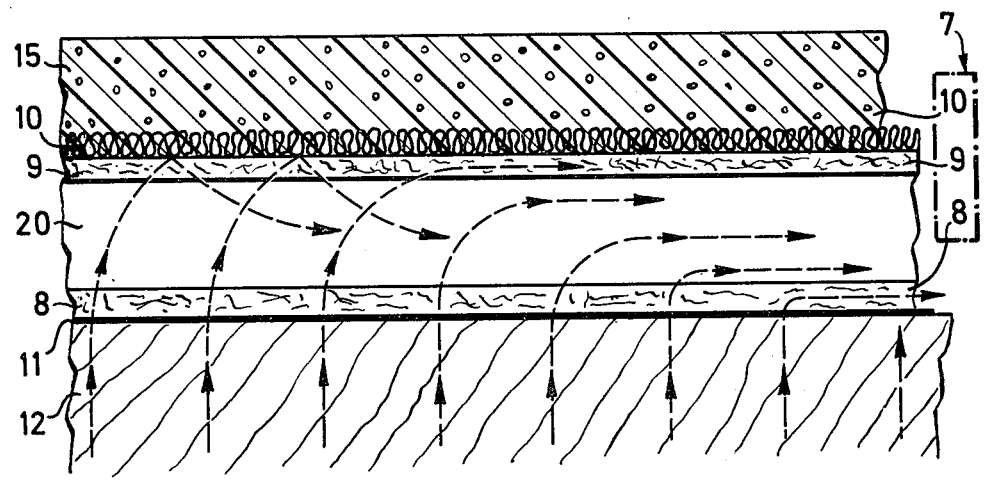
FIG. 7 shows a longitudinal section along the plane indicated by VII—VII in FIG. 6, through the embodiment shown in the latter.
Figure 8:
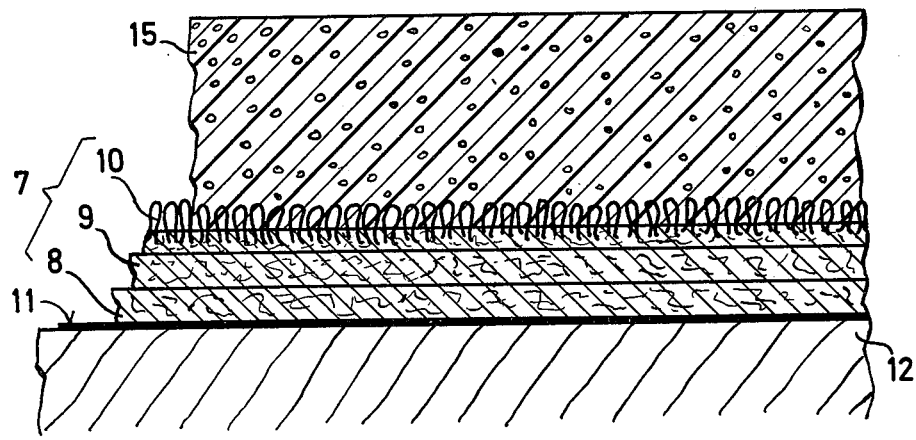
FIG. 8 shows a longitudinal section similar to that of FIG. 7 but along the plane indicated by VIII—VIII in FIG. 6, through the embodiment shown in this figure.

After the prepolymer material has cured forming the plastic layer 14, the cannula 13 is withdrawn from the base layer 7 and the ventilation channel 20 shown in FIGS. 6 and 7 remains. Arrows in FIGS. 6 and 7 indicate how perspiration and transpiration fluid are transported from the skin 11, mainly through the innermost ply 8 but also through the middle textile ply 9 which is not impregnated by plastic, towards the ventilation channel 20 so that they are removed from there, by means of external air flowing through the channel 20, from the surface of the body and out of the bandage.

Figure 9:
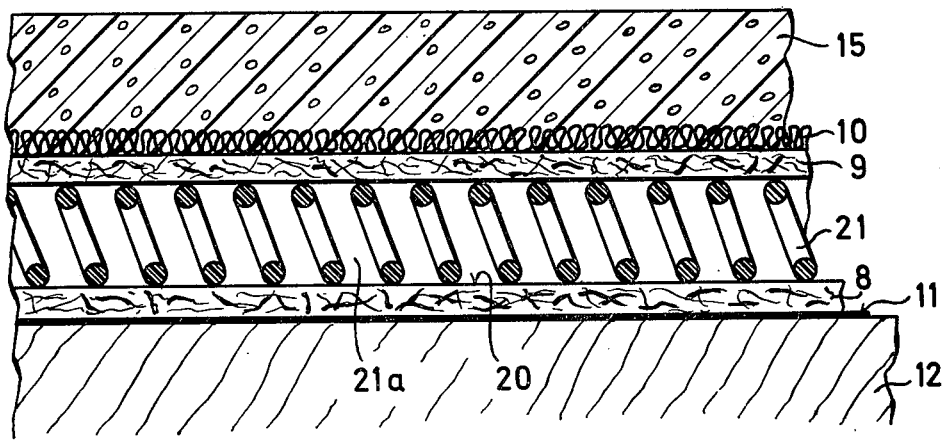
FIG. 9 shows the partial view of a longitudinal section, similar to that of FIG. 7, through a further embodiment of the rigid supporting bandage according to the invention.

The embodiment shown in FIG. 9 of the rigid supporting bandage according to the invention only differs from that according to FIGS. 3 to 8 in that, in place of the cannula 13, a plastic coil 21 having rather stiff turns in the manner of a helical spring is embedded between the innermost textile ply and the middle textile ply (8 and 9 respectively); sufficiently wide interspaces 21a remain between the windings of the coil in order to ensure the passage of transpiration fluid and perspiration from the skin into the interior of the ventilation channel 20.

It is not so critical in this embodiment that the prepolymer material should cure so rapidly that there is only just time for it to penetrate the outermost textile ply 10 of loose fabric. Rather, in this embodiment, it can also penetrate at least partially into the middle fabric ply 9 and even penetrate right through it in places, without thereby substantially restricting the functioning of the ventilation channel 20.

Figure 10:
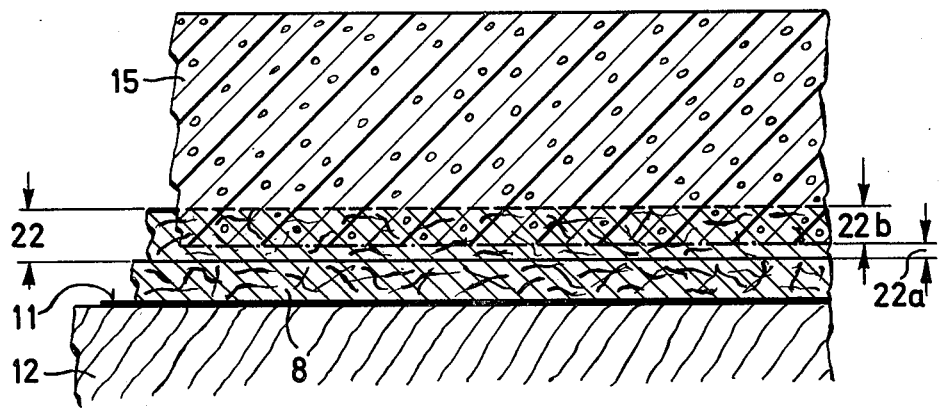
FIG. 10 shows the partial view of a longitudinal section through a yet further embodiment similar to that shown in FIG. 7; and finally

In the embodiment shown in FIG. 10 the base layer 7 comprises only the innermost ply 8 and the outer ply 22 which preferably is somewhat thicker. The thickness of this layer is adjusted to the rate of curing of the prepolymer material in such a way that the zone 22a adjacent to the inner ply 8 is not penetrated by prepolymer material which, rather, is only able to penetrate through the outer zone 22b of the textile ply 22, before it is cured.

Figure 11:
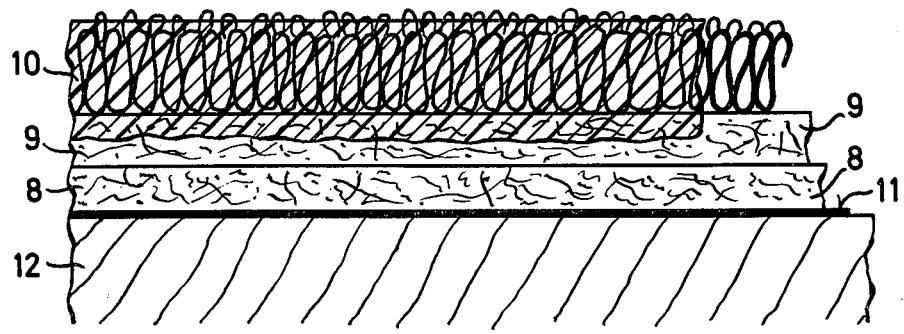
FIG. 11 shows a partial view in longitudinal section of a further modified embodiment similar to that in FIG. 7.

Finally, FIG. 11 shows a similar embodiment in which the thickness of the textile plies 8, 9 and 10 and the mesh-width of the outermost ply 10 as well as the rate of curing and the quantity of prepolymer material applied are matched to one another in such a way that the prepolymer material is just able completely to penetrate through the wide-meshed ply 10 and perhaps still to penetrate just into the outermost region of the closer-meshed ply 9, the plastic composition being just able, after curing, to fill the meshes of the outer textile ply 10 so that, at the time, the textile ply 10 impregnated with plastic forms the outermost layer of the bandage.

The supporting power of such a bandage is, of course, lower and it is therefore advantageously used as a sheet-like part of a bandage.

When applying the prepolymer layer it is also possible, in a manner which is in itself known, to use a sleeve or shell 23 which is merely indicated in FIG. 4 and which is taken off or drawn off the bandage after the plastic has completely cured.

A small pocket 25 with a window 26, for example of Plexiglas, which can serve to carry instructions for the doctor in charge, can be embedded on the outside of the plastic layer.

In the following text the making of a rigid supporting bandage according to the invention, such as is shown in the drawing, is described in more detail by several illustrative embodiments.

EXAMPLE 1

Figure 3:
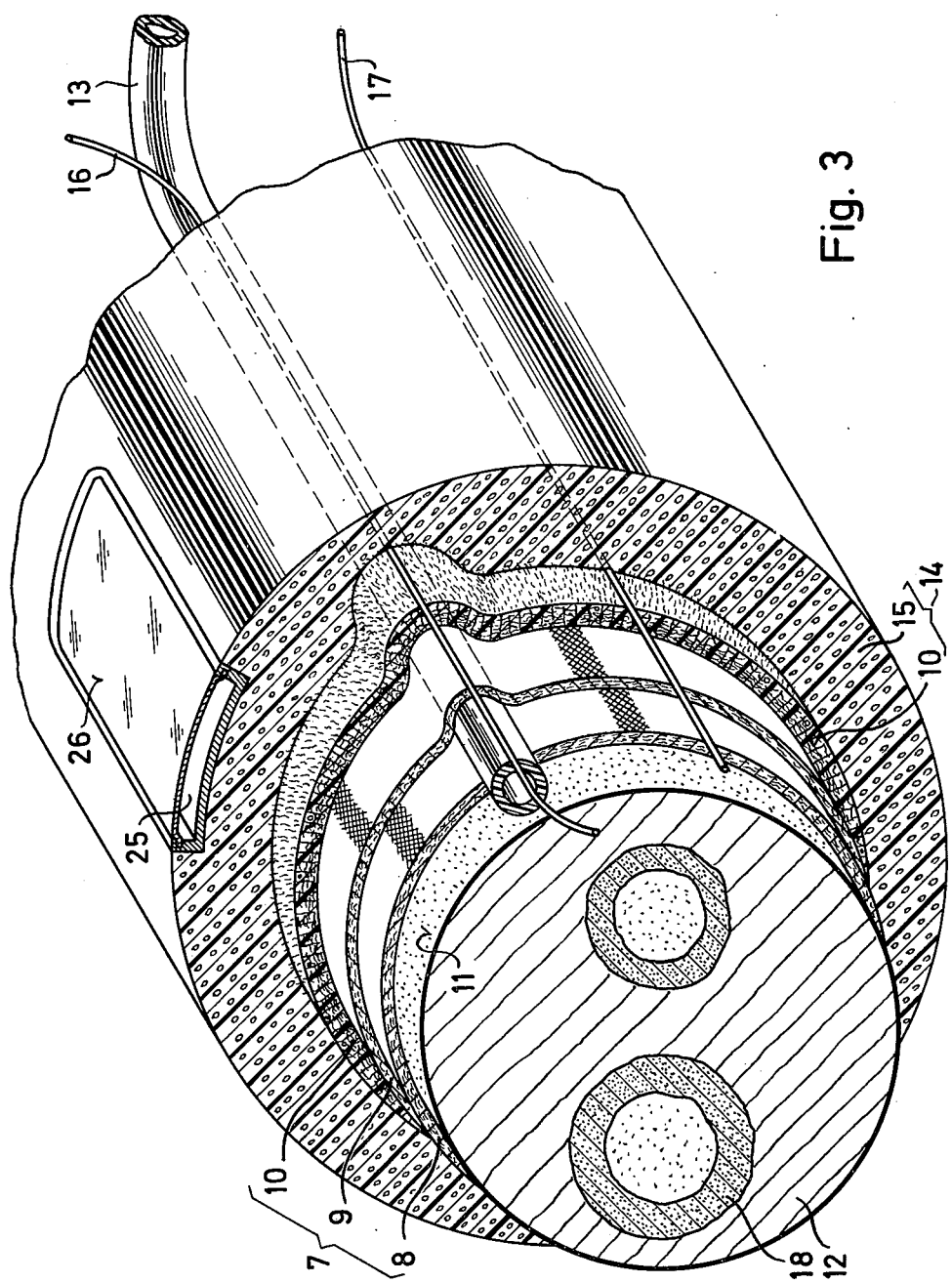
FIG. 3 shows a partial view of a slightly differently equipped embodiment in a perspective representation which is cut open stepwise along cutting planes which lie approximately in the plane indicated by III—III in FIG. 1 or parallel thereto.

For preparing a brachiocubital supporting bandage on an arm having an outside length of 70 cm, an inside length of 58 cm measured from the shoulder insertion or armpit to the wrist and an upper arm thickness of 9 cm, the intention being to obtain a rectangular fixation of the elbow joint and a fixation of the metacarpal joint and the basal phalangeal joints, an inner dense fabric tubing 8 is first pulled over the skin of the arm without any special prior preparation, a second similar fabric tubing 9 is pulled over the first and several, preferably two to three, means of passage in the form of cannulae 13 are then inserted between the two fabric tubings, as shown in FIG. 3, in the place and position which they are intended to take up in the finished supporting bandage. The cannulae 13 are firmly retained in their position by the elastic stretching of the second textile tubing 9, which is brought about in the first place or increased by their insertion.

Each of the two fabric tubings consists of knitted cotton stretch-fabric tubing of the single interlock type weighing 170 g/m$^2$ and has a length of approx. 72 cm in the unstretched state, a diameter of 10.5 cm and a weight of 28.8 g. A third loose textile stretch-tubing 10 which consists of loose knitted cotton fabric tubing weighing 105 g/m$^2$ and has, in the unstretched state, a length of 85 cm, a diameter of 8 cm and a weight of 14.45 g is now pulled in the same manner over the outer dense textile tubing 9. Two self-adhesive nylon strings 16 and 17 of high tensile strength are placed, as a means for tearing open the bandage onto the textile ply 10 in the longitudinal direction of the part of the body and are firmly held in position by means of adhesive tapes. A solution of adhesive or a pre-finish of the nylon thread, which becomes self-adhesive at a later stage, can also be used in place of adhesive tape.

When the various components of the textile carrier complex are applied step-wise, care must be taken that sufficient carrier material projects, everywhere on the outside of the supporting bandage to be applied which material is not covered by the reactive plastic mixture afterwards but can be folded later on over the end of the plastic shell or be cut off the finished bandage. It is not always necessary to provide a padding between two of these textile carrier plies; usually the entirety of the various textile plies alone suffices for satisfactory padding over any points of the body which protrude and are thus subject to the risk of pressure. In special cases a padding material (cottonwool, molleton, synthetic materials etc.) are inserted between two textile carrier plies and are held in position by the elasticity of the latter. Thus, the therapist remains free to decide where and how much padding is needed for the particular individual case.

For this purpose it is also possible to apply, on top of the textile ply 10 mentioned afore, a further second similar textile ply with interposed pads and then to fit the nylon threads 16 and 17 thereon. Care should also be taken that the means of tearing open the bandage protrude far enough from the layer of curing plastic mixture to be applied that, after the supporting bandage has been finished, this can easily be torn open by gripping the means of opening either by forming a loop or by winding it around, and thus fixing it to, a hard elongate object (scissor handle, bandage forceps and the like).

The prepolymer material is now applied. This is carried out by simple casting, if appropriate by foaming, manually or with the aid of an application tool, for example a multi-component mixing spray gun with a metering valve. A sleeve or shell described in connection with FIG. 4 or similar removable aids can also be used.

The prepolymer material consists of the following components: (all percentage data denote percent by weight);

Prepolymer component A: 360 g of a mixture of 81.5% of branched polyol from the sorbitol group (OH number 490, $OH_f = 7$) and 18.5% of fluorotrichloromethane, Prepolymer component B: 3.6 g of a tertiary amine accelerator (premixed in A); and Prepolymer component C: 400 g of a mixture of 80% of 2,4-diisocyanato-toluene and 20% of 2,6-diisocyanato-toluene as the prepolymer component in 28% strength sorbitol (OH number 491).

The indicated total amount of 763.6 g is rather generous for the supporting bandage of the structure and dimensions of this Example. The mixing time is 20 seconds and the pot life is 80 to 100 seconds, that is to say the application must take place rapidly and the prepolymer material just penetrates through the loose textile ply 10. After approximately 8 to 10 minutes it is fully cured and can subsequently be subjected to a full load.

Each cannula of polyvinyl chloride of the grade 43.0 g per meter weighs 34.4 g at a length of 80.0 cm and an outer diameter of 8.0 mm.

Each nylon tear string weighs only 0.56 g and has a length of 80.0 cm and a diameter of 1.0 mm.

When two dense textile plies and two loose textile plies, three cannulae and three tearing "wires" are used the total supporting bandage including the cured plastic composition weighs 955 g. After curing, the three cannulae are removed and the total weight of the finished bandage is then 852 g.

The following are further examples of prepolymer material:

EXAMPLE 2

Prepolymer component A: 300 g of an unsaturated polyester resin mixture composed of propylene glycol, maleic acid and phthalic acid (molar ratio 1:1:1);

Prepolymer component B: 12 g of a mixture of 50% of cyclohexanol peroxide and 50% of a phlegmatizing(desensitizing) adduct (amounting to about 4% of A and premixed in A); and Prepolymer component C: 12 g of a mixture of 4% of cobalt octoate and 96% of styrene (amounting to about 4% of A).

EXAMPLE 3

Prepolymer component A: 300 g of unsaturated polyester resin mixture composed of propylene glycol, maleic acid and phthalic acid (as in Example 2);

Prepolymer component B: 12 g of a mixture of 50% of benzoyl peroxide and 50% of a stabiliser adduct (corresponding to about 4% of A), premixed with A; and Prepolymer component C: 13.5 g of a mixture of 8% of dimethylamine and 92% of styrene (corresponding to about 4.5% of A).

The prepolymer component C is admixed in the course of 45 seconds to the mixture of the components A and B and the total mixture is then applied. It hardens in appoximately 8–10 minutes.

EXAMPLE 4

Prepolymer component A: 300 g of a mixture of 88% of a branched polyol from the sorbitol group (OH number approximately 480) and 12% of fluorotrichloromethane, premixed;

Prepolymer component B: 4 g of a tertiary amine accelerator, premixed in A; and

Prepolymer component C: 360 g of a mixture of 76% of 2,4-di-isocyanatotoluene and 24% of 2,6-diisocyanatotoluene as the prepolymer component in 28% strength sorbitol (OH number 485).

The prepolymer component C is mixed into the components A and B for approximately 20 seconds. Subsequently the prepolymer mixture is applied. The pot life is approximately 90 seconds. After 8 to 10 minutes the prepolymer is fully cured and can be subjected to a full load.

EXAMPLE 5

Prepolymer component A: 95 parts of 1,1,3-trihydroxyphenyl-propane (OH number 370);

Prepolymer component B: 24 parts of trichlorofluoromethane;

Prepolymer component C: 2 parts of 1-methyl-4-dimethylamino-ethyl-piperazine;

Prepolymer component D: 1 part of an oxyalkylene derivative of alkylsiloxane; and Prepolymer component E: 92 parts of polyphenylmethane polyisocyanate.

Before use all the components are thoroughly mixed for about 30 seconds and then applied. The curing time is approximately 10 minutes.

Special adjuvants, stabilisers, activator systems, inhibitor systems, anti-static agents, elastomers, protective agents against radiation, particularly protective agents against UV, or anti-ageing agents, curing agents and/or plasticisers can be added to the groups of plastic mixtures listed in the Examples, in order to obtain special properties which determine the external or internal behaviour of the plastic layer.

These special additives are optional; they do not affect the properties, according to the invention, of the supporting bandage as such, that is to say as a support-giving, immobilising and protective hard structure with physiological regulation of the part of the body under the bandage, Occasionally, however, these substances are desired, especially for the following special purposes:

1. improving the impact strength (addition of elastomer)
2. raising the ignition temperature (addition of a flame-proofing agent)
3. reducing the burning time (addition of a flame-proofing agent)
4. influencing the buyer psychologically (addition of a dye-stuff)
5. improving the anti-static properties (addition of anti-static agents) and finally
6. improving the protection against radiation (for example UV absorbers) as a precaution against destruction of the plastic shell by solar radiation or UV light.

The properties of the individual plastic mixtures, above all the pot life, the curing time, the latent period until full load can be applied and the degree of hardness can be altered within usually wide limits by varying the metering, the detailed composition of any accelerator systems, the activator systems, the additions of curing agent and the above-mentioned modifiers, in a manner which is in itself well known for curable plastics.

EXPLANATORY REMARKS ON THE VENTILATION SYSTEM (MEANS OF PASSAGE) ACCORDING TO THE INVENTION

In the following text the ventilation system of the supporting bandage according to the invention is explained in more detail. The form of application which is most usual is selected for describing the breathing system of this supporting bandage.

Since the innermost textile ply of the base layer rests directly on the surface of the skin of the part of the body it acts like a semi-permeable sponge or a filter paper, which sucks up the products of transpiration, perspiration and other skin metabolism, binds them partially and discharges the major part of the substances absorbed, above all gases and volatile substances, in the direction of the open ends of the respiration channels.

The heat generated by the general metabolism in the particular part of the body and the largely gaseous end products of the metabolism pass through the innermost textile ply of the base layer; the liquid phases are further distributed two-dimensionally over the base layer by capillary forces between the microscopic textile fibres and emerge at the front ends of the supporting bandage as a result of the pressure gradient from the surface of the skin to the ventilation channel. This occurs because the warmer air in the channel is lighter and migrates along the surface of the ventilation channel, which is largely heat-insulated by the plastic layer, in the direction of lower pressure and colder air, that is to say to the ends of the ventilation channels, which are open outwards. As a result of the heat gradient and pressure gradient the largely gaseous metabolic end products produced in the supporting bandage are in a sense conveyed outwards by self-ventilation.

Since the entire surface of the skin in the region of the supporting bandage is surrounded by a textile ply the liquid and gaseous secretion products are uniformly passed on outwards. This prevents the collection of water of condensation in the heat-insulated ventilation channel covered by the plastic and thus prevents excessive cooling due to evaporation restricted to certain regions of the bandage. This ensures a relatively constant temperature over the entire surface of the part of the body as well as a physiologial environment which makes it possible to avoid neuralgias and other pathological conditions.

Above the "bandaged" part of the body, which is covered by a largely insulating supporting bandage, an almost physiological environment of evaporation, above all of water vapour, transpiration (electrolytes from perspiration) and heat regulation is achieved, on the one hand, by the combination of "ventilation channel/outer opening for ventilation" and, on the other hand, by the system which equilibrates the environment of the surface of the skin (i.e. by innermost textile ply); thus the part of the body enclosed in the supporting bandage according to the invention is in an environment which is similar to that of everyday clothing and is hence substantially a physiological environment.

I claim:

1. A rigid supporting bandage being applied in situ for fixing and repositioning a part of the live body which is at least partially covered with skin, which bandage comprises
   a. a flexible base layer of textile material adapted to lie innermost on the body part to be fixed and repositioned, and being adapted to the shape of said body part,
   b. an outer layer of hard self-cured synthetic polymer resin on the outside of said bandage, and
   c. an intermediate layer on top of said base layer and underneath said layer of polymer resin, and consisting essentially of several plies of meshes of textile material filled with the same hard polymer resin which constitutes said outer layer;
   at least the innermost ply of meshes of said base layer being free from said hard polymer resin,
   said base layer having at least one front end uncovered by said intermediate and outer layers, and containing channels which open at said at least one front end to the outside of said bandage, said channels being covered, on the side thereof toward said body part, by said innermost polymer resin-free ply of meshes of said base layer.

2. A bandage as described in claim 1, wherein said channels are surrounded on all sides by textile material which is free from said polymer.

3. A bandage as described in claim 1, wherein the hard polymer resin is selected from cold-catalysed polyacrylate casting resin, acrylonitrile/butadiene/styrene polymer, polyacetal resin, acrylonitrile/styrene polymer, epoxide casting resin, epoxide foamed plastic, polyurethane polymer and polyurethane foamed plastic.

4. A bandage as described in claim 1, wherein the outermost ply of textile fabric facing the outer layer has so large a mesh width that it facilitates penetration of and intimate contact with the hard polymer resin layer.

5. A bandage as described in claim 1, wherein the channels for the respiration of the skin are accommodated between said innermost ply free from polymer resin and an adjacent outer ply of the base layer free from or penetrated by said hard polymer resin.

6. A bandage as described in claim 5, wherein the channels contain small tubes or rods which can be removed from the channels and are composed of a synthetic polymer material non-combinable with the hard polymer resin.

7. A bandage as described in claim 6, wherein said non-combinable synthetic polymer material is selected from polyvinyl chloride, polyethylene and polypropylene.

8. A bandage as described in claim 7, wherein the channels contain synthetic polymer bodies in the shape of a coil.

9. A bandage as described in claim 1, wherein the combined layers are translucent to X-rays and ionising rays to the extent of at least 50 to 80% or more.

10. A bandage as described in claim 1, wherein the hard polymer resin layer is adapted for being cut through by a pocket knife or a metal spatula or paper scissors.

11. A bandage as described in claim 1, wherein the outermost ply of the basic layer carries at least one wire which preferably extends in the longitudinal direction of the part of the body, and consists of a metal, a polymer thread or a thread of textile material of adequate tensile strength, and by means of which the polymer resin containing layers can be severed.

12. A bandage as described in claim 1, wherein at least the innermost ply of the base layer is close-meshed.

13. A bandage as described in claim 12, wherein said innermost layer consists of knitted cotton fabric.

14. A bandage as described in claim 1, wherein the outermost ply of the textile fabric layer consists of a wide-meshed woven or knitted fabric of cotton or woven fabric of synthetic fibre material.

15. A bandage as described in claim 1, wherein the thickness of the outer hard polymer resin layer is at least 1 mm.

16. A bandage as described in claim 1, wherein, on the surface of the outer layer, a small pocket or small compartment is fitted which consists of transparent resin and into which a card giving information on the wearer of the supporting bandage can be inserted.

17. A bandage as described in claim 1, wherein a padding material is accommodated between the body surface and the base layer or between the base and the intermediate textile fabric layers, this padding material being loosely held between the textile fabric layers or being applied to one of the textile fabric layers for preventing the formation of pressure sores, which may be caused by the supporting bandage, on the part of the body.

18. A bandage as described in claim 1, wherein, for the purpose of protection against external radiation, one or more additives are admixed to the polymer resin layer of the bandage or wherein an absorbent intermediate layer is inserted in the bandage so that a bandaged part of the body will be substantially protected against said external radiation.

19. A method for applying a supporting bandage in situ on a part of a live body, which part is at least partially covered by skin, for fixing and repositioning said body part, which method comprises:

i. placing on or about said body part a flexible base layer of textile material having several plies of meshes one of which plies is placed innermost on and adapted to the shape of said body part;

ii. applying on top of said base layer an intermediate layer consisting of several plies of meshes of textile material but leaving at least one front end of said base layer uncovered;

iii. inserting small tubes or rods of a synthetic polymer material into the base layer intermediate at least the innermost ply or several plies of meshes thereof, and a next adjacent outer ply of said base layer, said tubes or rods extending in a plane or planes parallel or tangential to the outside surface of said body part and parallel to said intermediate layer, and protruding from at least one front end of said base layer uncovered by said intermediate layer;

iv. applying about said intermediate layer a self-curing hardenable prepolymer material having a curing time such that it will penetrate during curing into and through said intermediate layer filling the meshes of the latter, down to or into the outermost ply or plies of said base layer but leaving the innermost layer thereof unimpregnated; said synthetic polymer material constituting said tubes or rods being non-combining with said prepolymer material or the hardened polymer therefrom.

v. withdrawing said small tubes or rods from said base layer after said prepolymer has penetrated the intermediate layer and has fully hardened.

20. A method as described in claim 19, wherein said prepolymer material is hardenable in half an hour or more rapidly.

21. A method as described in claim 19, wherein said small tubes or rods are of polyvinyl chloride, polyethylene or polypropylene.

* * * * *